United States Patent [19]

Schwertfeger et al.

[11] Patent Number: 6,159,539
[45] Date of Patent: *Dec. 12, 2000

[54] PROCESS FOR PREPARING ORGANICALLY MODIFIED AEROGELS AND USE THEREOF

[75] Inventors: Fritz Schwertfeger, Frankfurt; Andreas Zimmermann, Griesheim, both of Germany

[73] Assignee: Hoeschst Aktiengesellschaft, Frankfurt, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/981,802
[22] PCT Filed: Jul. 2, 1996
[86] PCT No.: PCT/EP96/02894
  § 371 Date: Jan. 8, 1998
  § 102(e) Date: Jan. 8, 1998
[87] PCT Pub. No.: WO97/03017
  PCT Pub. Date: Jan. 30, 1997

[30] Foreign Application Priority Data

Jul. 10, 1995 [DE] Germany .............. 195 25 021

[51] Int. Cl.[7] .............. B01D 7/00; B32B 21/02; B01J 12/00; C01B 33/12
[52] U.S. Cl. .............. 427/220; 516/101; 428/405; 423/338
[58] Field of Search .............. 252/315.2, 315.6; 516/100, 101; 428/405; 427/220; 423/338

[56] References Cited

U.S. PATENT DOCUMENTS

| 2,978,298 | 4/1961 | Wetzel et al. ............... 252/315.6 |
| 4,400,561 | 8/1983 | Mitchell et al. ............... 568/902 |
| 4,954,327 | 9/1990 | Blount ............... 252/315.6 |
| 5,110,784 | 5/1992 | Williams et al. ............... 502/401 |
| 5,548,051 | 8/1996 | Michalczyk et al. ............... 528/15 |
| 5,565,142 | 10/1996 | Deshpande et al. ............... 252/315.2 |
| 5,795,556 | 8/1998 | Jansen et al. ............... 423/338 |

FOREIGN PATENT DOCUMENTS

0658513 A1  6/1995  European Pat. Off.

OTHER PUBLICATIONS

Journal of Liquid Chromatography, vol. 11, No. 16, pp 3375–3384, 1988, month unknown.

Primary Examiner—Richard D. Lovering
Assistant Examiner—Daniel S. Metzmaier
Attorney, Agent, or Firm—Frommer Lawrence & Haug LLP

[57] ABSTRACT

The inventive process concerns the preparation of organically modified aerogels and their use.

The process the invention comprises:
  a) introducing a siliceous lyogel or hydrogel,
  b) optionally subjecting the gel prepared in a) to complete or partial solvent exchange with an organic solvent,
  c) reacting the gel obtained in step a) or b) with at least one silylation agent,
  d) optionally washing the silylated gel obtained in step c) with an organic solvent, and
  e) drying the gel obtained in step c) or d) subcritically, which comprises reacting in step c) the gel obtained in step a) or b) with at least one chlorine-free silylation agent.

15 Claims, No Drawings

PROCESS FOR PREPARING ORGANICALLY MODIFIED AEROGELS AND USE THEREOF

RELATED APPLICATION

This application is filed under 35 U.S.C. §371 and claims priority to PCT Application No. PCT/EP96/02894 filed Jul. 7, 1996, which claims priority to German Application No. 19525021.4 filed Jul. 5, 1995.

BACKGROUND OF THE INVENTION

1. Field of the Invention

The invention relates to a process for preparing organically modified $SiO_2$ aerogels and their use.

2. Description of the Related Art

Aerogels, in particular those having porosities above 60% and densities below 0.6 g/cm³, have an extremely low thermal conductivity and are therefore used as heat insulation material, such as described in EP-A-0 171 722.

SUMMARY OF THE INVENTION

Aerogels in the broad sense, i.e. in the sense of "gel having air as dispersion medium", are prepared by drying a suitable gel. The term "gel" in this sense includes aerogels in the narrower sense, xerogels and cryogels. A dried gel is termed an aerogel in the narrower sense here if the liquid of the gel is removed at temperatures above the critical temperature and starting from pressures above the critical pressure. If, in contrast, the liquid of the gel is removed subcritically, for example with formation of a liquid-vapor interface, the resulting gel is frequently also termed xerogel. It must be noted that the gels according to the invention are aerogels, in the sense of gel having air as dispersion medium. Since these gels are prepared by subcritical drying, they could also be described as xerogels, however.

$SiO_2$ aerogels can be prepared, for example, by acid hydrolysis of tetraethyl orthosilicate in ethanol. In the course of the hydrolysis, a gel is formed whose structure is determined, inter alia, by the temperature, the pH and the duration of the gelation process. However, the gel structure generally collapses during drying of the wet gels, since the capillary forces occurring during drying are extremely strong. The collapse of the gel can be prevented by carrying out the drying above the critical temperature and critical pressure of the solvent. Since the liquid/gaseous phase boundary disappears in this range, the capillary forces are also absent and the gel does not change during drying, i.e. the gel also does not shrink during drying. Preparation processes based on this drying technique are disclosed, for example, by EP-A-0 396 076 or WO 92/03378. However, this technique requires, for example when ethanol is used, a temperature of about 240° C. and pressures of over 60 bar. Although exchanging ethanol by $CO_2$ prior to drying lowers the drying temperature to approximately 30° C., the pressure required is then over 70 bar.

An alternative to the above drying is offered by a process for subcritical drying of $SiO_2$ gels if these are reacted with a chlorine-containing silylation agent prior to drying. The $SiO_2$ gel can be obtained in this case by means of water, for example by acid hydrolysis of tetraalkoxysilanes, preferably tetraethoxysilane (TEOS), in a suitable organic solvent, preferably ethanol. After exchanging the solvent for a suitable organic solvent, in a further step, the resulting gel is reacted with a chlorine-containing silylation agent. As silylation agent, use is preferably made of methylchlorosilanes ($Me_{4-n}SiCl_n$ where n=1 to 3), on account of their reactivity.

The resulting $SiO_2$ gel which is modified on the surface by methylsilyl groups can then be air-dried from an organic solvent. By this means aerogels having densities below 0.4 g/cm and porosities above 60% can be attained.

The preparation process based on this drying technique is described in detail in WO 94/25149.

Furthermore, the above-described gels can be admixed with tetraalkoxysilanes in the alcoholic aqueous solution prior to drying and aged in order to increase the gel network strength, as disclosed, for example, in WO 92/20623.

However, the tetraalkoxysilanes used as starting materials in the above-described processes represent an extraordinarily high cost factor.

A considerable reduction in costs can be achieved by using waterglass as starting material for preparing the $SiO_2$ gels. For this purpose, for example, from an aqueous waterglass solution, with the use of an ion-exchange resin, a silicic acid can be prepared which polycondenses to form an $SiO_2$ gel by addition of a base. After exchanging the aqueous medium for a suitable organic solvent, in a further step, the resulting gel is then reacted with a chlorine-containing silylation agent. As silylating agent, use is likewise preferably made here of methylchlorosilanes ($Me_{4-n}SiCl_n$ where n=1 to 3) on account of their reactivity. The $SiO_2$ gel formed in this case which is modified on the surface by methylsilyl groups can then likewise be air-dried from an organic solvent. The preparation process based on this technique is disclosed by DE-A-4 342 548.

However, silylation using chlorine-containing silylation agents unavoidably produces, in very large amounts, hydrogen chloride (HCl) and a multiplicity of associated by-products. The particularly corrosion-resistant production plants which are required owing to the formation of very large amounts of hydrogen chloride (HCl) are very expensive. The safety hazard associated with the formation of very large amounts of HCl gas further requires highly complex equipment and is thus likewise very cost-intensive.

An alternative to the above-described silylation using methylchlorosilanes ($Me_{4-n}SiCl_n$ where n=1 to 3) is the use of chlorine-free silylation agents of the formula III:

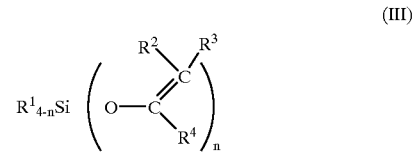

(III)

where

R¹ is in each case an identical or different unbranched or branched $C_1$–$C_6$-alkyl radical, cyclohexyl radical or phenyl radical, R², R³ and R⁴ are, identically or differently, hydrogen atoms, unbranched or branched $C_1$–$C_6$-alkyl radicals, cyclohexyl radicals or phenyl radicals, and n=1, 2 or 3.

One representative of these silylation agents is isopropeneoxytrimethylsilane. In the course of silylation it eliminates acetone as the sole by-product. This avoids the formation of hydrogen chloride (HCl) and the associated safety hazard. The preparation process based on this silylation technique is described in detail in German patent application 195 02 453.

However, since the above-described chlorine-free silylation agents may only be synthesized experimentally in a highly complex manner and are not currently available on an industrial scale, the problems described above of the very high process costs are not solved by these extraordinarily expensive chlorine-free silylation agents.

OBJECT OF THE INVENTION

The object of the present invention was therefore to provide a process for preparing organically modified $SiO_2$ aerogels which does not have the disadvantages which result from the prior art, such as, for example, on the one hand the formation of elimination products or even reaction products which have both safety and processing problems and, on the other hand, the use of silylating agents which are difficult to synthesize and not currently available on an industrial scale, which themselves give rise to extraordinarily high process costs.

DETAILED DESCRIPTION OF THE INVENTION

This object is achieved by a process for preparing organically modified aerogels, in which a) a siliceous lyogel or hydrogel is introduced,
b) the gel prepared in step a) is optionally subjected to complete or partial solvent exchange with an organic solvent,
c) the gel obtained in step a) or b) is reacted with at least one silylation agent,
d) the silylated gel obtained in step c) is optionally washed with an organic solvent, and
e) the gel obtained in step c) or d) is dried subcritically, which comprises reacting in step c) the gel obtained in step a) or b)
with at least one chlorine-free silylation agent of the formula I and/or II,

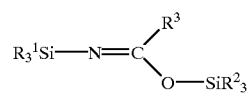

(I)

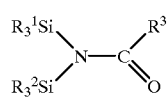

(II)

where
$R^1$, $R^2$, $R^3$ independently of one another are, identically or differently, hydrogen atoms, unbranched or branched $C_1$–$C_6$-alkyl, cyclohexyl or phenyl radicals.

In a preferred embodiment, in step a), a siliceous lyogel is introduced which is obtainable by hydrolysis and condensation of Si alkoxides in an organic solvent containing water. The Si alkoxide used is a tetraalkoxysilane, preferably tetraethoxy- or tetramethoxysilane. The organic solvent in this case is preferably an alcohol, particularly preferably ethanol or methanol to which up to 20% by volume of water can be added.

In the hydrolysis and condensation of the Si alkoxides in an organic solvent containing water, in a single- or two-stage step, acids and/or bases can be added as catalysts.

In a particularly preferred embodiment, in step a) a siliceous hydrogel is introduced which is prepared by bringing an aqueous waterglass solution to a pH ≤ 3 using an acid ion-exchange resin or a mineral acid, polycondensing the resulting silicic acid by adding a base to give an $SiO_2$ gel and, if a mineral acid was used, optionally washing the gel with water to be free of electrolyte. In this process, generally, sodium waterglass and/or potassium waterglass is used. The ion-exchange resin used is preferably an acid resin, those which contain sulfonic acid groups being particularly suitable. If mineral acids are used, hydrochloric acid and sulfuric acid are especially suitable.

The base used is preferably $NH_4OH$, NaOH, KOH, $Al(OH)_3$ and/or colloidal silicic acid. If a mineral acid was used, the $SiO_2$ gel produced using the base should optionally be washed with water to be free of electrolyte. Preferably, the gel is washed here until the effluent wash water has the same electrical conductivity as demineralized water. Prior to washing, the gel is preferably aged, that is generally at 0 to 150° C., preferably at 80 to 130° C., and at a pH of 4 to 11, preferably 4 to 9. The time for this is generally 10 seconds to 48 hours, preferably 10 seconds to 5 hours.

Step a) is generally carried out at a temperature between the freezing point of the solution and the boiling point of the solvent or solvent mixture.

As organic solvents in step b), use is generally made of aliphatic alcohols, ethers, esters or ketones, or aliphatic or aromatic hydrocarbons. Mixtures of said solvents can also be used. Preferred solvents are methanol, ethanol, acetone, tetrahydrofuran, ethyl acetate, dioxane, n-hexane, n-heptane and toluene. Particularly preferably, acetone is used as solvent in step b).

In step c), the solvent-containing gel is reacted with at least one chlorine-free silylation agent of the formula I and/or II

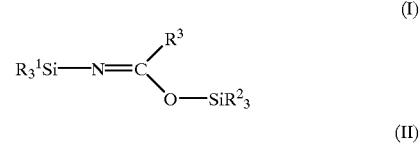

where
$R^1$, $R^2$, $R^3$ independently of one another are, identically or differently, hydrogen atoms, unbranched or branched $C_1$–$C_6$-alkyl, cyclohexyl or phenyl radicals.

Preferably, $R^1$ and $R^2$ are each, identically or differently, a methyl or ethyl group and $R^3$ is a hydrogen atom or a methyl group.

Particular preference is given to N,O-bis(trimethylsilyl) acetamide (formula I: $R^1 = R^2 = R_3 = CH_3$).

The reaction is preferably carried out at 0 to 100° C. in aqueous or completely or partially anhydrous organic solvent, those solvents preferably being used which are also used in the solvent exchange in step b). Particular preference is given to acetone.

The silylation can optionally be carried out using catalytic amounts of acid or base. Catalytic amounts means that the amount of acid or base is less than 1% by weight based on the wet gel. The acid used in this case is generally a customary acid such as HCl, $H_2SO_4$ or acetic acid, the base used is a customary base such as $NH_4OH$, NaOH, KOH or $Al(OH)_3$. However, trimethylchlorosilane (TMCS) is also suitable. If appropriate, the silylation can also be carried out under pressure, preferably up to 25 bar.

In the reaction of the gel with the chlorine-free silylation agents of the formula I and/or II according to the invention, neutral amides are formed.

When N,O-bis(trimethylsilyl)acetamide is used, acetamide is formed in this manner as elimination product, which is soluble in water and in the acetone which is preferably used.

Since the N,O-bis(trimethylsilyl)acetamide is a reactive silylation agent in the presence of water, at least a part of the complex and cost-intensive solvent exchange before the silylation can be dispensed with.

A further advantage of the process according to the invention is that, in the silylation with the chlorine-free silylation agents according to the invention, no HCl gas is formed, and therefore no corrosive, chlorine-containing byproducts are formed either.

In step d), the silylated gel can be washed with an organic solvent. As organic solvents, use is generally made of aliphatic alcohols, ethers, esters or ketones, or aliphatic or aromatic hydrocarbons. Mixtures of said solvents can also be used. Preferred solvents are methanol, ethanol, acetone, tetrahydrofuran, ethyl acetate, dioxane, n-hexane, n-heptane and toluene. Particularly preferably, acetone is used as solvent.

In step e), the washed gel is dried subcritically, preferably at temperatures of −30 to 200° C., particularly preferably 0 to 100° C., and at pressures of preferably 0.001 to 20 bar, particularly preferably 0.01 to 5 bar, in particular 0.1 to 2 bar, for example by radiant, convection and/or contact drying. The drying is preferably continued until the gel has a residual solvent content of less than 0.1% by weight. The aerogels obtained in the drying are permanently hydrophobic.

In another embodiment, the gel, depending on application, can be further subjected to network reinforcement prior to the silylation. This is achieved by reacting the resulting gel with a solution of an orthosilicate which is capable of condensation of the formula $R^1_{4-n}Si(OR^2)_n$, preferably an alkyl orthosilicate and/or aryl orthosilicate, where n=2 to 4 and $R^1$ and $R^2$ independently of one another are hydrogen atoms, unbranched or branched $C_1$–$C_6$-alkyl, cyclohexyl or phenyl radicals, or by reacting the gel with an aqueous silicic acid solution.

For many applications of aerogels in which further components are added prior to the surface modification, it is particularly advantageous to be able to avoid a strongly acidic silylation, as in the case of chlorosilanes, without impairing the function of the surface modification.

The aerogels obtainable by the process according to the invention are preferably used as heat insulation materials.

The process according to the invention is described in more detail below with reference to working examples, without being restricted thereto, however.

The thermal conductivities in the examples are measured by a resistance wire method (see, for example, O. Nielsson, G. Rüschenpöhler, J. Groß, J. Fricke, High Temperatures—High Pressures, Vol. 21, 267–274 (1989)).

EXAMPLES

Example 1

1 l of a sodium waterglass solution (having an $SiO_2$ content of 8% by weight and an $Na_2O:SiO_2$ ratio of 1:3.3) is stirred together with 0.5 l of an acid ion exchange resin (styrenedivinylbenzenecopolymer containing sulfonic acid groups, commercially available under the name ®Duolite C20) until the pH of the aqueous solution is 2.7. The ion-exchange resin is then filtered off and the aqueous solution is adjusted to a pH of 5.0 using 1 molar NaOH solution. The resulting hydrogel is then aged for 5 hours at 85° C. and the water is then extracted with acetone until the water content in the gel is below 1% by weight. The acetone-containing gel is then silylated with 5% by weight of N,O-bis(trimethylsilyl)acetamide, 0.1% by weight of TMCS and an equimolar amount of water (based on N,O-bis(trimethylsilyl)acetamide) at 50° C. for 3 hours (5% by weight of N,O-bis(trimethylsilyl)acetamide and 0.1% by weight of TMCS based on the wet gel) and then washed with 3 l of acetone. The gel is air-dried (3 hours at 40° C., then 2 hours at 50° C. and 12 hours at 150° C.).

The transparent aerogel thus obtained has a density of 0.2 g/cm³. The BET specific surface area is 500 m²/g. The λ value is 0.018 W/mK.

Example 2

The hydrogel is prepared as described in Example 1. The resulting hydrogel is then aged at 85° C. for 5 hours and then the water is extracted with acetone until the water content in the gel is 25% by weight. The acetone-containing gel is then silylated with 5% by weight of N,O-bis(trimethylsilyl)acetamide and 0.1% by weight of TMCS at 50° C. for 3 hours (5% by weight N,O-bis(trimethylsilyl)acetamide and 0.1% by weight of TMCS based on the wet gel) and then washed with 3 l of acetone. The gel is air-dried (3 hours at 40° C., then 2 hours at 50° C. and 12 hours at 150° C.).

The transparent aerogel thus obtained has a density of 0.25 g/cm³. The BET specific surface area is 560 m²/g. The λ value is 0.025 W/mK.

What is claimed is:

1. A process for preparing organically modified aerogels, in which
   a) a siliceous lyogel or hydrogel is introduced,
   b) the gel prepared in step a) is optionally subjected to partial solvent exchange with an organic solvent,
   c) the gel obtained in step a) or b) is reacted in the presence of water with at least one silylation agent, and wherein the water content is about 1% to 25% by weight based on the wet gel,
   d) the silylated gel obtained in step c) is optionally washed with an organic solvent, and
   e) the gel obtained in step c) or d) is dried subcritically, which comprises reacting in step c) the gel obtained in step a) or b) in the presence of water with at least one chlorine-free silylation agent of the formula I and/or II,

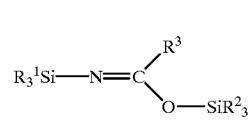

(I)

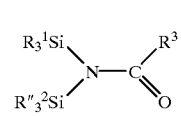

(II)

where $R^1$, $R^2$, $R^3$ independently of one another are, identically or differently, hydrogen atoms, unbranched or branched $C_1$–$C_6$-alkyl, cyclohexyl or phenyl radicals.

2. The process as claimed in claim 1, wherein a siliceous lyogel is introduced which is obtained by hydrolysis and condensation of Si alkoxides in an organic solvent containing water.

3. The process as claimed in claim 1, wherein a siliceous hydrogel is introduced, the siliceous hydrogel is obtained by adjusting an aqueous waterglass solution to a Ph≦3 using an acid ion-exchange resin or a mineral acid, polycondensing the resulting silicic acid to form an $SiO_2$ gel by adding a base and, if a mineral acid was used, washing the gel with water to be free of electrolyte.

4. The process as claimed in claim 3, wherein the base is selected from the group consisting of $NH_4OH$, NaOH, KOH, $Al(OH)_3$, colloidal silicic acid or mixtures thereof.

5. The process as claimed in claim 1, wherein the $SiO_2$ gel obtained in step a) is aged at 0 to 150° C. and a pH of 4 to 11 for a period of 10 seconds to 48 hours.

6. The process as claimed in claim 1, wherein, as organic solvent in step b) is methanol, ethanol, acetone, tetrahydrofuran, ethyl acetate, diocane, n-hexane, n-heptane, toluene or mixtures thereof.

7. The process as claimed in claim 1, wherein the gel obtained in step a) or b) is reacted, prior to the silylation, with a solution of an orthosilicate capable of condensation of the formula $R^1_{4-n}Si(OR^2)_n$, where n=2 to 4 and $R^1$ and $R^2$ independently of one another are hydrogen atoms, unbranched or branched $C_1$–$C_6$-alkyl, cyclohexyl or phenyl radicals, or is reacted with an aqueous silicic acid solution.

8. The process as claimed in claim 21 wherein the orthosilicate is an alkylorthosilicate and/or aryl orthosilicate.

9. The process as claimed in claim 1, wherein, in step c), the solvent-containing gel is reacted with at least one chlorine-free silylation agent of the formula I and/or II, where $R^1$ and $R^2$ are each identically or differently a methyl or ethyl group and $R^3$ is a hydrogen atom or a methyl group.

10. The process as claimed in claim 9, wherein the solvent-containing gel is reacted in step c) with N,O-bis(trimethylsilyl)acetamide.

11. The process as claimed in claim 1, wherein the reaction in step c) is carried out in the presence of catalytic amounts of acid or base.

12. The process as claimed in claim 1, wherein the reaction in step c) is carried out in an organic solvent at a temperature in the range from 0 to 100° C.

13. The process as claimed in claim 1, wherein the silylation is carried out under pressure.

14. The process as claimed in claim 1, wherein the resulting silylated gel is washed in step d) with a protic or aprotic solvent, before it is dried in step e).

15. The process as claimed in claim 11, wherein, in step e) the silylated gel is dried at −30 to 200° C. and 0.001 to 20 bar.

* * * * *